US006262201B1

(12) United States Patent
Welch et al.

(10) Patent No.: US 6,262,201 B1
(45) Date of Patent: Jul. 17, 2001

(54) ARYL SUBSTITUTED METALLOCENE CATALYSTS AND THEIR USE

(75) Inventors: M. Bruce Welch, Bartlesville, OK (US); Erik Licht; Helmut G. Alt, both of Bayreuth (DE)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/334,852

(22) Filed: Jun. 17, 1999

Related U.S. Application Data

(60) Provisional application No. 60/090,037, filed on Jun. 19, 1998.

(51) Int. Cl.[7] .................................. C08F 4/58; C08F 4/16
(52) U.S. Cl. .......................... 526/127; 526/160; 526/943; 556/11; 556/53; 502/152
(58) Field of Search ...................... 526/160, 943, 526/348, 352, 127; 556/11, 53; 502/152

(56) References Cited

U.S. PATENT DOCUMENTS

| | | | |
|---|---|---|---|
| 5,075,467 | 12/1991 | Desobry | 556/53 |
| 5,191,132 | 3/1993 | Patsidis et al. | 585/375 |
| 5,483,014 | 1/1996 | Turner et al. | 526/113 |
| 5,498,581 | 3/1996 | Welch et al. | 502/102 |
| 5,700,748 | 12/1997 | Murray | 502/102 |
| 5,780,659 | 7/1998 | Schmid et al. | 556/11 |
| 5,866,497 | 2/1999 | Murray | 509/150 |

OTHER PUBLICATIONS

Naga et al., Stereochemical control in propylene with non––bridged metallocene dichloride/methylaluminoxane, Polymer Papers, vol. 39 (13), 2703–2708, Jun. 1998.*

Jagy et al., para–Fluoro benzyl substituted bis(indenyl) metallocene as catalysts precursors in ethene polymerization, JOMC 553 (1998) 173–178, Feb. 1998.*

\* cited by examiner

*Primary Examiner*—David W. Wu
*Assistant Examiner*—R. Harlan
(74) *Attorney, Agent, or Firm*—Edward L. Bowman

(57) ABSTRACT

Substituted metallocenes which have a substituent selected from the group consisting of aryl alkyl, aryl alkyl silyl, and aryl silyl groups, catalyst systems resulting from the combination of such metallocenes and a cocatalyst, and for producing olefins using such catalyst systems.

19 Claims, No Drawings

ARYL SUBSTITUTED METALLOCENE CATALYSTS AND THEIR USE

This application claims the benefit of U.S. Provisional Application No. 60/090037, filed Jun. 19, 1998, the disclosure of which is incorporated herein by reference.

BACKGROUND OF THE INVENTION

U.S. Pat. No. 5,324,800 discloses that certain substituted metallocenes when used in catalyst systems for producing olefin polymers produce higher activity than when one uses an unsubstituted metallocene such as bis(cyclopentadienyl) zirconium dichloride. The patent contains the broad statement that included among the possible substituents are various hydrocarbyl radicals having 1 to 20 carbon atoms. Arylalkyl radicals are recited as one example of such hydrocarbyl radicals. There is, however, only one arylalkyl substituted metallocene actually named, i.e. bis(beta-phenylpropyl cyclopentadienyl) zirconium dimethyl. See column 5, lines 23 and 24. Example 4 of the patent might conceivably have used bis(beta-phenylpropylcyclopentadienyl) zirconium dichloride; however, even that is just an assumption based on the fact that the symbols used in Example 4 were the same as those used in connection with the naming of the dimethyl metallocene in column 5, lines 23 and 24. From the nomenclature used in the patent it is assumed that in both of those metallocenes the substituted cyclopentadienyl group was 1-cyclopentadienyl-2-phenyl-2-methyl-ethane, that is to say that there were only two carbons separating tie cyclopentadienyl group and the phenyl group. Example 4 of that patent provides some evidence that that particular metallocene was slightly more than twice as active as the unsubstituted metallocene bis(cyclopentadienyl)zirconium dichloride.

The present inventors have since prepared the metallocenes bis(phenylmethylidene cyclopentadienyl) zirconium dichloride, bis(phenylethylidene cyclopentadienyl) zirconium dichloride, and bis (phenyl-n-propylidene cyclopentadienyl) zirconium dichloride, which could also be called bis(1-phenyl-3-cyclopentadienyl-n-propane) zirconium dichloride, and have used those metallocenes with an aluminoxane cocatalyst in the polymerization of olefins. It was observed that the activity increased as the length of the alkylidene group was increased. The first two named metallocenes gave activities that were much less than half of the activity of the later. It would therefor be logical to assume that the metallocene having the n-propylidene alkylene group connecting the phenyl and the cyclopentadienyl was more active than the metallocene of Example 4 of the above mentioned patent, said metallocene having only two carbons between the phenyl and the cyclopentadienyl rather than 3.

The applicants also prepared bis(phenyl-isopropylidene-cyclopentadienyl) zirconium dichloride, i.e. a metallocene in which the alkylene radical connecting the phenyl and the cyclopentadienyl was 1,1-dimethyl methylene. That metallocene was of very low activity as compared to that of even bis(phenylmethylidene cyclopentadienyl) zirconium dichloride and bis(phenylethylidene cyclopentadienyl) zirconium dichloride. The metallocene had an activity of only about 5.8 kg of polyethylene per hour which is even lower than that reported for the unsubstituted cyclopentadienyl metallocene bis(cyclopentadienyl) zirconium dichloride. See U.S. Pat. No. 5,780,659 which shows that under substantially the same polymerization conditions bis(cyclopentadienyl) zirconium dichloride had an activity of about 136 kg of polyethylene per hour.

The present invention is based in part upon the discovery that different aryl alkyl, aryl alkyl silyl, or aryl silyl substituted metallocenes produce unexpected effects when used with a cocatalyst in the polymerization of olefins.

Thus an object of the present invention is to provide certain metallocenes having unexpected properties. Another object is to provide processes for the polymerization of olefins using such metallocenes.

SUMMARY OF THE INVENTION

In accordance with the present invention, there is provided new substituted metallocenes which have a substituent selected from the group consisting of aryl alkyl, aryl alkyl silyl, and aryl silyl groups.

In accordance with another aspect of the present invention there are provided catalyst systems resulting from the combination of such metallocenes with a suitable cocatalyst.

In accordance with yet another aspect of the present invention there is provided methods for producing olefins using such catalyst systems.

DETAILED DESCRIPTION OF THE INVENTION

In accordance with the present invention there is provided unbridged bis metallocenes in which each ligand has the formula

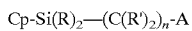

$$Cp\text{-}Si(R)_2\text{—}(C(R')_2)_n\text{-}A$$

wherein Cp is selected from cyclopentadienyl, 3-methylcyclopentadienyl, and 1-indenyl, each R can be the same or different and is an alkyl radical having 1 to 6 carbon atoms, each R' can be the same or different and is selected from hydrogen and alkyl radicals having 1 to 6 carbon atom, A is an aryl radical, i.e. a cyclic compound having conjugated unsaturation, and is n is 0 to 5 or

$$Cp\text{—}(C(R')_2)_n\text{-}A$$

wherein Cp is selected from cyclopentadienyl, 3-methylcyclopentadienyl, 1-indenyl, A is an aryl radical as defined above, and n is 1 to 5, except when Cp is cyclopentadienyl and A is phenyl then R' is not methylene, dimethyl methylene, or 2-methyl ethylene which is connected such that the phenyl is also bonded to the 2 carbon of the 2-methyl ethylene. Some examples of A include phenyl, 4-methylphenyl, 1-indenyl, 9-fluorenyl, naphthyl, 4-fluorophenyl, 3,5-dimethylphenyl, and the like.

The inventive metallocenes are produced by reacting the necessary ligands using techniques known in the art. Unbridged mixed metallocenes can be prepared by reacting unsubstituted half sandwich cyclodienyl $ZrCl_3$ with the lithium salt of a selected aryl substituted cyclodienyl compound. For example cyclopentadienyl $ZrCl_3$ can be reacted with the lithium salt of cyclopentadienyl methylidene phenyl to yield the metallocene (phenyl methylidene cyclopentadienyl) (cyclopentadienyl) $ZrCl_2$.

Aryl substituted cyclodienyl compounds needed to produce the inventive metallocenes can be produced by reacting an omega bromo alkyl aryl compound or an omega bromo alkyl silyl aryl compound or an omega bromo silyl aryl compound with cyclopentadienyl sodium. A similar technique can yield aryl substituted fluorenyl compounds. 1-Aryl substituted indenyl compounds can be produced by reacting indenyl lithium with aryl 1-haloalkanes or aryl dialkyl chloro silanes. Aryl indenyl compounds with the aryl group attached at the 2 position can be produced by reacting 2-indanone with omega phenylalkyl magnesium bromide in diethyl ether, then hydrolyzing, and finally dehydrogenating using p-toluenesufonic acid.

The aryl substituted metallocenes can be used for the polymerization. The inventive catalyst systems are particularly useful for the polymerization of alpha-olefins having 2 to 10 carbon atoms. Examples of such olefins include ethylene, propylene, butene-1, pentane-1, 3-methylbutene-1, hexene-1, 4-methylpentene-1, 3-methylpentene-1, heptene-1, octene-1, decene-1, 4,4-dimethyl-1-pentane, 4,4-diethyl-1-hexene, 3,4-dimethyl-1-hexene, and the like and mixtures thereof. The catalysts are also useful for preparing copolymers of ethylene and propylene and copolymers of ethylene or propylene and a higher molecular weight olefin. Monomers such as styrene and butadiene are also useful.

Polymerizations with the inventive catalyst can be carried out under a wide range of conditions depending upon the particular metallocene employed and the particular results desired. The inventive catalyst systems are considered useful for polymerization conducted under solution, slurry, or gas phase reaction conditions. Typically the inventive metallocene would be used with a suitable cocatalyst.

Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion cocatalyst, an example of such is disclosed in U.S. Pat. No. 5,155,080, e.g. using triphenyl carbenium tetrakis (pentafluorophenyl) boronate. Another example would be the use a mixture of triethylaluminum and dimethylfluoroaluminum such as disclosed by Zambelli et al, *Macromolecules,* 22, 2186 (1989). In such counter anion systems the cocatalyst can be viewed as an ion-exchange compound comprising a cation which will irreversibly react with as least one ligand contained in the metallocene and a non-coordination anion which is ether a single coordination complex comprising a plurality of lipophilic radicals covalently coordinated to and shielding a central formally charge-bearing metal or metalloid atom or an anion comprising a plurality of boron atoms such as polyhedral boranes, carboranes, and metallacarboranes.

The currently most preferred cocatalyst is an aluminoxane. Such compounds include those compounds having repeating units of the formula

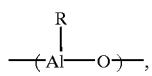

where R is generally a hydrocarbyl group having 1 to 5 carbon atoms. The organo aluminoxane component used in preparing the inventive solid catalyst system include oligomeric aluminum compounds having repeating units of the formula

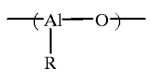

Some examples are often represented by the general formula $(-AlR-O-)_n$ or $R(-AlR-O-)_nAlR^2$. In the general aluminoxane formula R is preferably a $C_1-C_5$ alkyl radical, for example, methyl, ethyl, propyl, butyl or pentyl and "n" is an integer from 1 to about 50. Most preferably, R is methyl and "n" is at least 4.

Aluminoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an aluminoxane. Generally the reaction of an aluminum alkyl with a limited amount of water is postulated to yield a mixture of the linear and cyclic species of the aluminoxane. Aluminoxanes, also sometimes referred to as poly (hydrocarbyl aluminum oxides) are well known in the art and are generally prepared by reacting an hydrocarbylaluminum compound with water. Such preparation techniques are disclosed in U.S. Pat. Nos. 3,242,099 and 4,808,561, the disclosures of which are incorporated herein by reference. The currently preferred aluminoxane cocatalysts are prepared either from trimethylaluminum or triethylaluminum and are sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In a particular preferred embodiment, the inventive metallocene can be employed in combination with a solid organoaluminoxane which is substantially insoluble in the polymerization diluent under particle form polymerization conditions. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640. Still another technique involves contacting a dried support such as silica with trimethylaluminum and then adding water to form a solid containing pendant aluminoxy groups, such cocatalysts are sometimes referred to as partially hydrated trimethylaluminum or PHT for short.

Still another technique of producing a solid cocatalyst involves contacting an organoaluminoxane with an organic borane compound free of acidic hydrogen as taught U.S. Pat. No. 5,354,721, the disclosure of which is incorporated herein by reference. Yet another technique involves contacting an organoaluminoxane with an organoboron compound having boron acid functionality, i.e.—BOH, as taught in U.S. Pat. No. 5,414,189, the disclosure of which is incorporated herein by reference.

The currently preferred technique for preparing the solid organoaluminoxy cocatalyst involves contacting an organic solution of an organoaluminoxane optionally containing trialkylaluminums with a suitable organoboroxine compound as taught in U.S. Pat. No. 5,411,925, the disclosure of which is incorporated herein by reference.

When the polymerizations are carried out in the presence of liquid diluents obviously it is important to use diluents which do not have an adverse effect upon the catalyst system. Typical liquid diluents include propane, butane, isobutane, pentane, hexane, heptane, octane, cyclohexane, methylcyclohexane, toluene, xylene, and the like. Typically the polymerization temperature can vary over a wide range, temperatures typically would be in a range of about −60° C. to about 300° C., more preferably in the range of about 20° C. to about 160° C. Typically the pressure of the polymerization would be in the range of from about 1 to about 500 atmospheres or even greater. The inventive catalyst system is particularly useful for polymerizations carried out under particle form, i.e., slurry-type polymerization conditions.

The polymers produced with the catalysts herein disclosed have a wide range of uses that will be apparent to those skilled in the art from the physical properties of the respective polymers. Applications such as molding, films, adhesives, and the like are indicated.

A further understanding of the present invention and its objects and advantages will be provided by the following examples.

EXAMPLE 1

A series of mixed unbridged metallocenes having one ligand which had aryl substitution were prepared and then evaluated for their effectiveness in the polymerization of ethylene. The metallocene were each combined with a 30 weight percent toluene solution of methylaluminoxane in amounts to yield a Zr/Al mole ratio of about 1/3000. Each resulting catalyst composition was then used within one hour in a polymerization. The polymerizations were conducted in a 1 liter autoclave reactor. The catalyst composition was added to 500 ml of pentane in the reactor. An ethylene pressure of 10 bar was applied to the contents of the reactor after the reactor reached 50° C. The contents of the reactor were stirred and the polymerization was allowed to continue for 1 hour at about 60° C. The reactor was then vented and the polymer was recovered and dried in a vacuum.

The results obtained are summarized below:

TABLE 1

| | Activity[b] $\left[\dfrac{\text{kg PE}}{\text{g Zr·h}}\right]$ | $\overline{M}_\eta$[c] [kg/mol] | DSC $T_m$ [° C.] $\Delta H_m$ [J/g] $\alpha$ [%][d] |
|---|---|---|---|
| 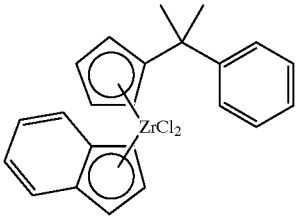<br>2 | 15.2 | 450 | 139.1<br>102.1<br>35.2 |
| 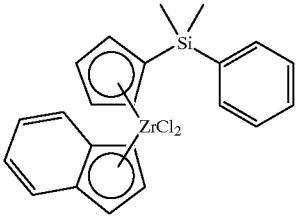<br>3 | 289 | 450 | 130.5<br>167.3<br>57.7 |
| 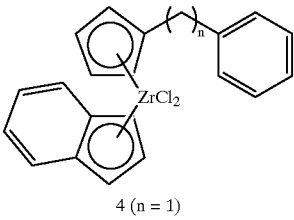<br>4 (n = 1) | 2887.8 | 500 | 127.0<br>170.3<br>58.7 |
| 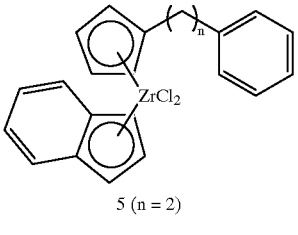<br>5 (n = 2) | 1899.2 | 640 | 139.7<br>152.6<br>52.6 |

TABLE 1-continued
| | Activity[b] $\left[\dfrac{\text{kg PE}}{\text{g Zr} \cdot \text{h}}\right]$ | $\overline{M}_\eta$[c] [kg/mol] | DSC $T_m$ [°C.] $\Delta H_m$ [J/g] $\alpha$ [%][d] |
|---|---|---|---|
| 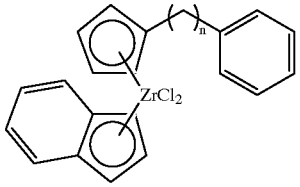 6 (n = 3) | 3534.0 | 630 | 138.4 140.0 48.3 |
| 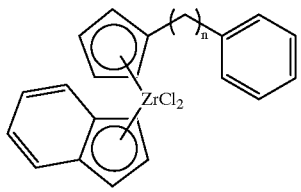 7 (n = 4) | 4508.7 | 610 | 132.5 148.1 51.1 |
| 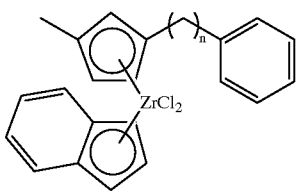 9a, b (n = 1) | 2986.0 | 560 | 137.8 152.5 52.6 |
| 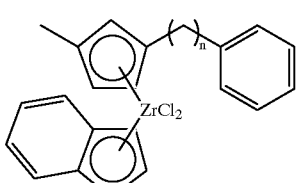 10a, b (n = 2) | 2676.0 | 600 | 136.5 138.5 47.8 |
| 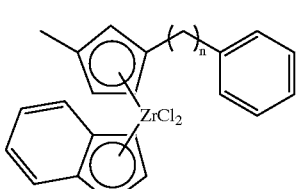 11a, b (n = 3) | 3579.0 | 420 | 139.7 137.4 47.4 |
| 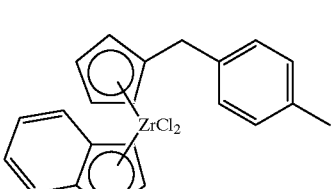 12 | 979.0 | 620 | 137.0 141.6 48.9 |

TABLE 1-continued

| | Activity[b] $\left[\dfrac{kg\ PE}{g\ Zr \cdot h}\right]$ | $\overline{M}_n$[c] [kg/mol] | DSC $T_m$ [° C.] $\Delta H_m$ [J/g] $\alpha$ [%][d] |
|---|---|---|---|
| 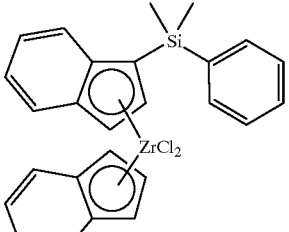 13a, b | 300 | 390 | 134.9 185.0 63.8 |
| 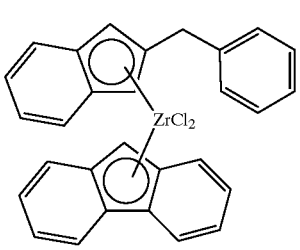 15 | 85.4 | 360 | 139.1 137.3 47.3 |

[a] $T_p = 60°$ C.; solvent: 500 ml pentane; 10 bar ethylene pressure.
[b] [M]/[Al] = 1:3000.
[c] Intrinsic viscosity.
[d] Degree of crystallinity relative to the fusion enthalpy of 100% crystalline polyethylene.

The results above reveal that the most active catalysts were catalysts 4; 5; 6; 7; 9a,b; 10a,b; and 11a,b, i.e. (phenyl methylidiene cyclopentadienyl) (indenyl) zirconium dichloride, (phenyl ethylidiene cyclopentadienyl) (indenyl) zirconium dichloride, (phenyl n-propylidene cyclopentadienyl) (indenyl) zirconium dichloride, (phenyl n-butylidene cyclopentadienyl) (indenyl) zirconium dichloride, (phenyl methylidiene 3-methylcyclopentadienyl) (indenyl) zirconium dichloride, (phenyl ethylidiene 3-methylcyclopentadienyl) (indenyl) zirconium dichloride, and (3-methyl phenyl n-propylidene cyclopentadienyl) (indenyl) zirconium dichloride, respectively. Note that the a,b denotes that the metallocenes were isomeric mixtures.

EXAMPLE 2

A series of bis(aryl substituted cyclodienyl) zirconium dichlorides were prepared and evaluated for their effectiveness as ethylene polymerization catalysts using the same procedure as described in Example 1. The results are shown in the following table. Here again the a,b indicates that the metallocene was an isomeric mixture.

TABLE 2

| | Activity[b] $\left[\dfrac{kg\ PE}{g\ Zr \cdot h}\right]$ | $\overline{M}_n$[c] [kg/mol] | DSC $T_m$ [° C.] $\Delta H_m$ [J/g] $\alpha$ [%][d] |
|---|---|---|---|
| 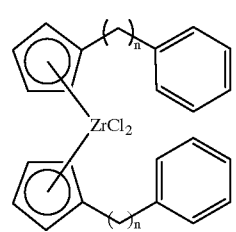 27 (n = 1) | 140.2 | 340 | 126.7 180.4 62.2 |

TABLE 2-continued
| | Activity[b] $\left[\dfrac{\text{kg PE}}{\text{g Zr}\cdot\text{h}}\right]$ | $\overline{M}_\eta$[c] [kg/mol] | DSC $T_m$ [° C.] $\Delta H_m$ [J/g] $\alpha$ [%][d] |
|---|---|---|---|
| 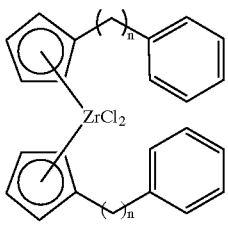<br>28 (n = 2) | 336.7 | 350 | 129.8<br>161.9<br>55.8 |
| 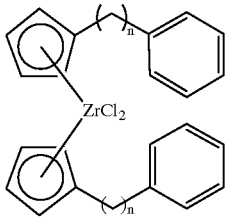<br>30 (n = 3) | 1506.0 | 390 | 136.8<br>155.1<br>53.5 |
| 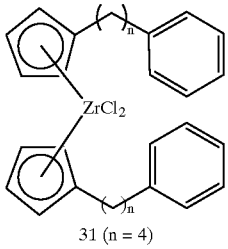<br>31 (n = 4) | 4970.0 | 270 | 140.0<br>152.0<br>52.4 |
| 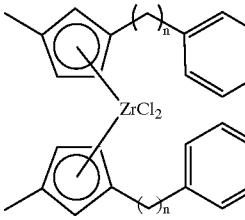<br>32a, b (n = 1) | 881.0 | 320 | 125.6<br>177.8<br>61.3 |
| 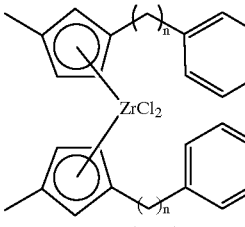<br>33a, b (n = 2) | 359.3 | 620 | 139.9<br>143.1<br>49.4 |

TABLE 2-continued
| Structure | Activity [kg PE / g Zr·h] | $\overline{M}_\eta$ [kg/mol] | DSC $T_m$ [°C] $\Delta H_m$ [J/g] $\alpha$ [%] |
|---|---|---|---|
| 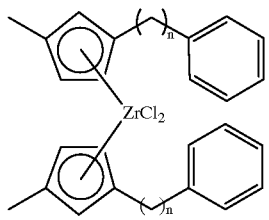 34a, b (n = 3) | 582.3 | 570 | 136.0<br>149.0<br>51.4 |
| 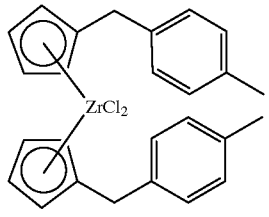 35 | 1880.9 | 310 | 133.1<br>150.6<br>52.0 |
| 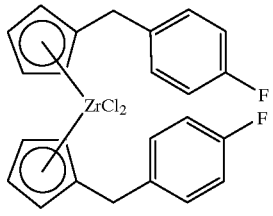 36 | 1784.0 | 340 | 134.1<br>152.3<br>52.5 |
| 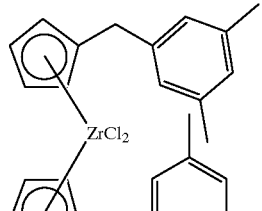 37 | 1120.4 | 590 | 130.0<br>168.8<br>58.2 |
| 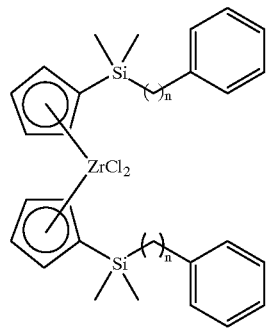 38 (n = 0) | 129.0 | 420 | 140.7<br>144.6<br>49.9 |

TABLE 2-continued
| | Activity[b] $\left[\frac{kg\ PE}{g\ Zr\cdot h}\right]$ | $\overline{M}_\eta$[c] [kg/mol] | DSC $T_m$ [° C.] $\Delta H_m$ [J/g] $\alpha$ [%][d] |
|---|---|---|---|
| 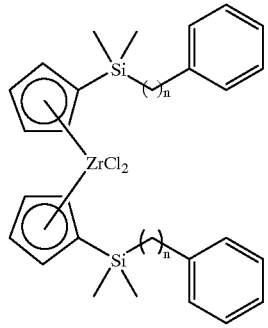<br>39 (n = 1) | 529.0 | 260 | 139.0<br>154.8<br>53.4 |
| 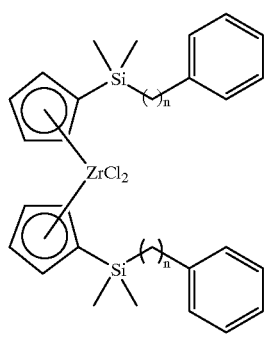<br>40 (n = 2) | 23.3 | 1050 | 135.1<br>120.2<br>41.5 |
| 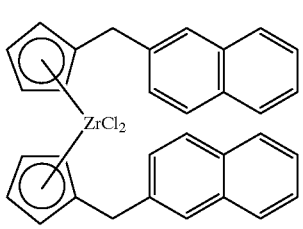<br>41 | 1020.1 | 490 | 130.4<br>133.0<br>45.9 |
| 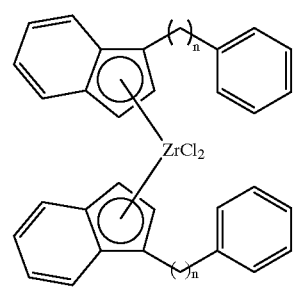<br>43a, b (n = 2) | 868.0 | 370 | 124.8<br>203.7<br>70.3 |

TABLE 2-continued
| | Activity[b] $\left[\dfrac{\text{kg PE}}{\text{g Zr} \cdot \text{h}}\right]$ | $\overline{M}_\eta$[c] [kg/mol] | DSC $T_m$ [° C.] $\Delta H_m$ [J/g] $\alpha$ [%][d] |
|---|---|---|---|
| 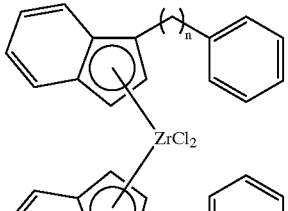 44a, b (n = 3) | 780.0 | 370 | 133.9 153.5 52.8 |
| 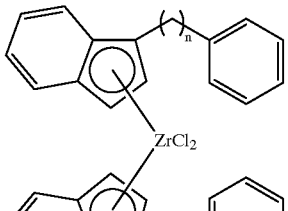 45a, b (n = 4) | 987.1 | 380 | 136.7 152.4 52.6 |
| 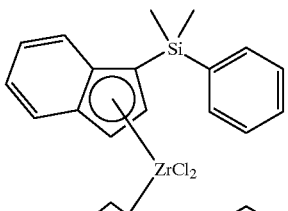 46a, b | 183.0 | 480 | 128.3 157.8 54.4 |
| 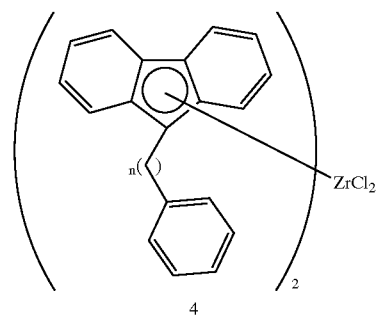 49 (n = 1) | 56.3 | 360 | 133.2 132.1 45.6 |

TABLE 2-continued

| | Activity [kg PE / g Zr·h] | $\overline{M}_\eta$ [kg/mol] | DSC $T_m$ [°C] $\Delta H_m$ [J/g] $\alpha$ [%] |
|---|---|---|---|
| 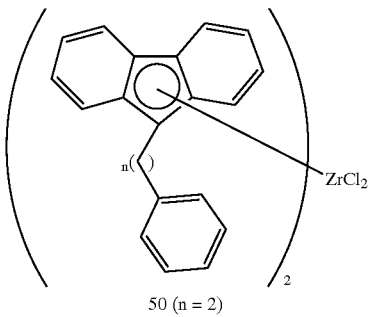 50 (n = 2) | 17.0 | 90 | 144.6 125.9 43.4 |
| 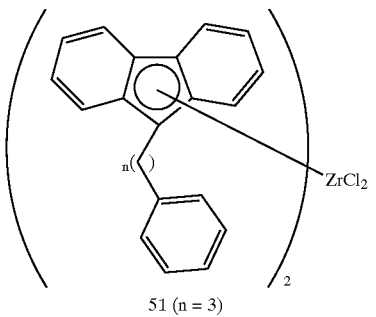 51 (n = 3) | 24.0 | 75 | 137.6 159.5 55.0 |
| 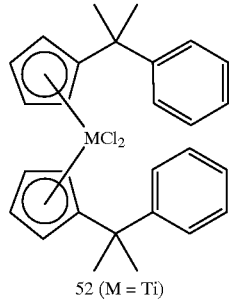 52 (M = Ti) | 7.6 | 130 | not determined |
| 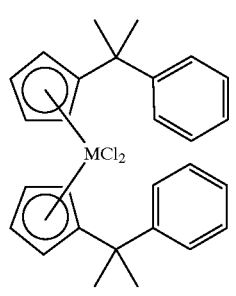 53 (M = Zr) | 5.8 | 300 | not determined |

The results show that the most active metallocenes were No.30, bis(phenyl n-propylidene cyclopentadienyl) zirconium dichloride, No. 31 bis(phenyl n-butylidene cyclopentadienyl) zirconium dichloride, No. 35 bis(4-methylphenyl methylidene cyclopentadienyl) zirconium dichloride, No. 36 bis(4-fluorophenyl methylidene cyclopentadienyl) zirconium dichloride, 37 bis(3,5-dimethylphenyl methylidene cyclopentadienyl) zirconium dichloride, and No. 41 bis(naphthyl methylidene cyclopentadienyl) zirconium dichloride.

That which is claimed is:

1. An unbridged sandwich bonded metallocene selected from the unbridged bis metallocenes in which each ligand has the formula

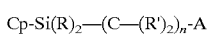

wherein Cp is selected from cyclopentadienyl, 3-methylcyclopentadienyl, and 1-indenyl, each R can be the same or different and is an alkyl radical having 1 to 6 carbon atoms, each R' can be the same or different and is selected from hydrogen and alkyl radicals having 1 to 6 carbon atom, A is an aryl radical, and n is 0 to 5 or

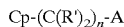
Cp-(C(R')$_2$)$_n$-A wherein Cp is selected from cyclopentadienyl, 3-methylcyclopentadienyl, 1-indenyl, A is an aryl radical, n is 1 to 5, and R' is as defined above, except when Cp is cyclopentadienyl and A is phenyl then R' is not methylene, dimethyl methylene or 2-methyl ethylene which is connected such that the phenyl is also bonded to the 2 carbon of the 2-methyl ethylene, and unbridged sandwich bonded metallocenes in which the two cyclodienyl ligands differ and wherein one of the cyclodienyl ligands is selected from those having the formula

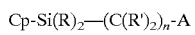
Cp-Si(R)$_2$—(C(R')$_2$)$_n$-A wherein Cp is selected from cyclopentadienyl, 3-methylcyclopentadienyl, and 1-indenyl, each R can be the same or different and is an alkyl radical having 1 to 6 carbon atoms, each R' can be the same or different and is selected from hydrogen and alkyl radicals having 1 to 6 carbon atom, A is a cyclic compound having conjugated unsaturation, and n is 0 to 5 or

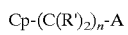
Cp-(C(R')$_2$)$_n$-A wherein Cp is selected from cyclopentadienyl, 3-methylcyclopentadienyl, 1-indenyl, A is an aryl radical, each R' can be the same or different and is selected from hydrogen and alkyl radicals having 1 to 6 carbon atoms, and n is 1 to 5.

2. A metallocene according to claim 2 selected from the group consisting of:
bis(phenyl ethylidene cyclopentadienyl) zirconium dichloride,
bis(phenyl n-propylidene cyclopentadienyl) zirconium dichloride,
bis(phenyl n-butylidene cyclopentadienyl) zirconium dichloride,
bis(phenyl methylidene 3-methylcyclopentadienyl) zirconium dichloride,
bis(phenyl ethylidene 3-methylcyclopentadienyl) zirconium dichloride,
bis(phenyl n-propylidene 3-methylcyclopentadienyl) zirconium dichloride,
bis(4-methylphenyl methylidene cyclopentadienyl) zirconium dichloride,
bis(4-fluorophenyl methylidene cyclopentadienyl) zirconium dichloride,
bis(3,5-dimethylphenyl methylidene cyclopentadienyl) zirconium dichloride,
bis(phenyl dimethylsilylene cyclopentadienyl) zirconium dichloride,
bis((1-phenyl)(2-cyclopentadienyl) dimethylsilylmethylidene)zirconium dichloride,
bis((1-phenyl)(3-cyclopentadienyl) dimethylsilylethylidene)zirconium dichloride
bis(naphthyl methylidene cyclopentadienyl) zirconium dichloride,
bis(phenyl ethylidene 1-indenyl) zirconium dichloride,
bis(phenyl propylidene 1-indenyl) zirconium dichloride,
bis(phenyl dimethylsilylene 1-indenyl) zirconium dichloride,
bis(phenyl methylidene 9-fluorenyl) zirconium dichloride,
bis(phenyl ethylidene 9-fluorenyl) zirconium dichloride,
bis(phenyl ethylidene 2-indenyl) zirconium dichloride,
bis(phenyl methylidene 2-indenyl)zirconium dichloride, and
bis(phenyl propylidene 9-fluorenyl) zirconium dichloride.

3. A metallocene according to claim 1 selected from the group consisting of:
(phenyl isopropylidene cyclopentadienyl) (indenyl) zirconium dichloride,
(phenyl dimethylsilyl cyclopentadienyl) (indenyl) zirconium dichloride,
(phenyl methylidene cyclopentadienyl) (indenyl) zirconium dichloride,
(phenyl ethylidene cyclopentadienyl) (indenyl) zirconium dichloride,
(phenyl propylidene cyclopentadienyl) (indenyl) zirconium dichloride,
(phenyl butylidene cyclopentadienyl) (indenyl) zirconium dichloride,
(phenyl methylidene 3-methylcyclopentadienyl) (indenyl) zirconium dichloride,
(phenyl ethylidene 3-methylcyclopentadienyl) (indenyl) zirconium dichloride,
(phenyl propylidene 3-methylcyclopentadienyl) (indenyl) zirconium dichloride,
(phenyl dimethylsilyl 1-indenyl) (indenyl) zirconium dichloride,
(4-methylphenyl methylidene cyclopentadienyl) (indenyl) zirconium dichloride, and
(phenyl methylidene 1-indenyl) (fluorenyl) zirconium dichloride.

4. A metallocene according to claim 1 selected from the group consisting of:
(phenyl methylidene cyclopentadienyl) (indenyl) zirconium dichloride, (phenyl ethylidene cyclopentadienyl) (indenyl) zirconium dichloride,(phenyl propylidene cyclopentadienyl) (indenyl) zirconium dichloride, and (phenyl butylidene cyclopentadienyl) (indenyl) zirconium dichloride.

5. A metallocene according to claim 1 selected from the group consisting of:
(phenyl methylidene 3-methylcyclopentadienyl) (indenyl) zirconium dichloride,
(phenyl ethylidene 3-methylcyclopentadienyl) (indenyl) zirconium dichloride, and
(phenyl propylidene 3-methylcyclopentadienyl) (indenyl) zirconium dichloride.

6. A metallocene according to claim 1 selected from the group consisting of:
bis( phenyl n-propylidene cyclopentadienyl zirconium dichloride, and
bis (phenyl n-butylidene cyclopentadienyl) zirconium dichloride.

7. A metallocene according to claim 1 selected from the group consisting of:
bis(4-methylphenyl methylidene cyclopentadienyl) zirconium dichloride, bis(4-fluorophenyl methylidene cyclopentadienyl) zirconium dichloride, and bis(3,5-dimethylphenyl methylidene cyclopentadienyl ) zirconium dichloride.

8. A catalyst composition useful for the polymerization of olefins comprising the product resulting from the combination of a metallocene with an organometallic cocatalyst, said metallocene being an unbridged sandwich bonded metallocene selected from the unbridged bis metallocenes in which each ligand has the formula $$Cp-Si(R)_2-(C-(R')_2)_n-A$$

wherein Cp is selected from cyclopentadienyl, 3-methylcyclopentadienyl, and 1-indenyl, each R can be the same or different and is an alkyl radical having 1to 6 carbon atoms, each R' can be the same or different and is selected from hydrogen and alkyl radicals having 1 to 6 carbon atom, A is an aryl radical, and n is 0 to 5 or $$Cp-(C(R')_2)_n-A$$

wherein Cp is selected from cyclopentadienyl, 3-methylcyclopentadienyl, 1-indenyl, A is an aryl radical, n is 1 to 5, and R' is as defined above, except when Cp is cyclopentadienyl and A is phenyl then R' is not methylene, dimethyl methylene or 2-methyl ethylene which is connected such that the phenyl is also bonded to the 2 carbon of the 2-methyl ethylene, and unbridged sandwich bonded metallocenes in which the two cyclodienyl ligands differ and wherein one of the cyclodienyl ligands is selected from those having the formula $$Cp-Si(R)_2-(C(R')_2)_n-A$$

wherein Cp is selected from cyclopentadienyl, 3-methylcyclopentadienyl, and 1-indenyl, each R can be the same or different and is an alkyl radical having 1 to 6 carbon atoms, each R' can be the same or different and is selected from hydrogen and alkyl radicals having 1 to 6 carbon atom, A is a cyclic compound having conjugated unsaturation, and n is 0 to 5 or $$Cp-(C(R')_2)_n-A$$

wherein Cp is selected from cyclopentadienyl, 3-methylcyclopentadienyl, 1-indenyl, A is an aryl radical, each R' can be the same or different and is selected from hydrogen and alkyl radicals having 1 to 6 carbon atoms, and n is 1 to 5.

9. A catalyst composition according to claim 8 wherein the metallocene is selected from the group consisting of: (phenyl methylidene 3-methylcyclopentadienyl) (indenyl) zirconium dichloride, (phenyl ethylidene 3-methylcyclopentadienyl) (indenyl) zirconium dichloride, and (phenyl propylidene 3-methylcyclopentadienyl) (indenyl) zirconium dichloride.

10. A catalyst composition according to claim 8 wherein the metallocene is selected from the group consisting of:

bis(phenyl n-propylidene cyclopentadienyl) zirconium dichloride, and bis(phenyl n-butylidene cyclopentadienyl) zirconium dichloride.

11. A catalyst composition according to claim 8 wherein the metallocene is selected from the group consisting of:

bis(4-methylphenyl methylidene cyclopentadienyl zirconium dichloride, bis(4-fluorophenyl methylidene cyclopentadienyl) zirconium dichloride, and bis(3,5-dimethylphenyl methylidene cyclopentadienyl) zirconium dichloride.

12. A process for producing a polymer comprising contacting at least one olefin under polymerization conditions with a catalyst composition resulting form the combination of a metallocene with an organometallic cocatalyst, said metallocene being an unbridged sandwich bonded metallocene selected from the unbridged bis metallocenes in which each ligand has the formula $$Cp-Si(R)_2-(C-(R')_2)_n-A$$

wherein Cp is selected from cyclopentadienyl, 3-methylcyclopentadienyl, and 1-indenyl, each By can be the same or different and is an alkyl radical having 1 to 6 carbon atoms, each R' can be the same or different and is selected from hydrogen and alkyl radicals having 1 to 6 carbon atom, A is an aryl radical, and n is 0 to 5 or $$Cp-(C(R')_2)_n-A$$

wherein Cp is selected from cyclopentadienyl), 3-methylcyclopentadienyl, 1-indenyl, A is an aryl radical, n is 1 to 5, and R' is as defined above, except when Cp is cyclopentadienyl and A is phenyl then R' is not methylene, dimethyl methylene or 2-methyl ethylene which is connected such that the phenyl is also bonded to the 2 carbon of the 2-methyl ethylene, and unbridged sandwich bonded metallocenes in which the two cyclodienyl ligands differ and wherein one of the cyclodienyl ligands is selected from those having the formula $$Cp-Si(R)_2-(C(R')_2)_n-A$$

wherein Cp is selected from cyclopentadienyl, 3-methylcyclopentadienyl, and 1-indenyl, each R can be the same or different and is an alkyl radical having 1 to 6 carbon atoms, each R' can be the same or different and is selected frown hydrogen and alkyl radicals having 1 to 6 carbon atom, A is a cyclic compound having conjugated unsaturation, and n is 0 to 5 or $$Cp-(C(R')_2)_n-A$$

wherein Cp is selected from cyclopentadienyl, 3-methylcyclopentadienyl, 1 -indenyl, A is an aryl radical, each R' can be the same or different and is selected from hydrogen and alkyl radicals having 1 to 6 carbon atoms, and n is 1 to 5.

13. A process according to claim 12 wherein ethylene is polymerized.

14. A process according to claim 13 wherein the cocatalyst is an alkylaluminoxane.

15. A process according to claim 14 wherein the metallocene is selected from wherein the metallocene is selected from the group consisting of (phenyl methylidene 3-methylcyclopentadienyl) (indenyl) zirconium dichloride, (phenyl ethylidene 3-methylcyclopentadienyl) (indenyl) zirconium dichloride, and (phenyl propylidene 3-methylcyclopentadienyl) (indenyl) zirconium dichloride.

16. A process according to claim 14 wherein the metallocene is selected from the group consisting of:

bis(4-methylphenyl methylidene cyclopentadienyl) zirconium dichloride, bis(4-fluorophenyl methylidene cyclopentadienyl) zirconium dichloride, and bis(3,5-dimethylphenyl methylidene cyclopentadienyl) zirconium dichloride.

17. A process according to claim 14 wherein the metallocene is selected from the group consisting of:

bis( phenyl n-propylidene cyclopentadienyl) zirconium dichloride, and bis(phenyl n-butylidene cyclopentadienyl) zirconium dichloride.

18. A process according to claim 14 carried out under slurry polymerization conditions.

19. A process according to claim 14 carried out under solution polymerization conditions.

* * * * *